United States Patent
Samain et al.

(10) Patent No.: US 9,358,187 B2
(45) Date of Patent: Jun. 7, 2016

(54) DEVICE FOR SELF-FOAMING OXIDATION DYEING, READY-FOR-USE SELF-FOAMING COMPOSITION AND METHOD FOR DYEING KERATINOUS FIBRES

(71) Applicant: L'Oreal, Paris (FR)

(72) Inventors: Henri Samain, Bievres (FR); Jean-Marc Ascione, Paris (FR); Maxime De Boni, Tokyo (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/354,499

(22) PCT Filed: Oct. 26, 2012

(86) PCT No.: PCT/EP2012/071253
§ 371 (c)(1),
(2) Date: Apr. 25, 2014

(87) PCT Pub. No.: WO2013/060838
PCT Pub. Date: May 2, 2013

(65) Prior Publication Data
US 2014/0305463 A1    Oct. 16, 2014

Related U.S. Application Data

(60) Provisional application No. 61/566,774, filed on Dec. 5, 2011.

(30) Foreign Application Priority Data

Oct. 26, 2011 (FR) ..................................... 11 59717

(51) Int. Cl.
| | | |
|---|---|---|
| *A61Q 5/10* | (2006.01) | |
| *A61K 8/04* | (2006.01) | |
| *A61K 8/31* | (2006.01) | |
| *A61K 8/365* | (2006.01) | |
| *A61K 8/19* | (2006.01) | |
| *A61K 8/22* | (2006.01) | |
| *A45D 7/04* | (2006.01) | |
| *A45D 19/02* | (2006.01) | |

(52) U.S. Cl.
CPC . *A61K 8/046* (2013.01); *A45D 7/04* (2013.01); *A45D 19/02* (2013.01); *A61K 8/19* (2013.01); *A61K 8/22* (2013.01); *A61K 8/31* (2013.01); *A61K 8/315* (2013.01); *A61K 8/365* (2013.01); *A61Q 5/10* (2013.01); *A61K 2800/882* (2013.01)

(58) Field of Classification Search
CPC ......... A61Q 5/10; A61K 8/315; A61K 8/365; A61K 8/19; A61K 8/22; A61K 8/046; A61K 8/31; A61K 2800/882; A45D 19/02; A45D 7/04
USPC ...................... 8/405, 406, 410, 411, 412, 477
See application file for complete search history.

(56) References Cited

U.S. PATENT DOCUMENTS

| | | | |
|---|---|---|---|
| 6,740,129 B2 * | 5/2004 | Tsujino et al. | ..................... 8/405 |
| 8,187,338 B2 * | 5/2012 | Lane et al. | ......................... 8/405 |
| 2003/0084517 A1 | 5/2003 | Tsujino | |
| 2004/0002550 A1 | 1/2004 | Mercurio | |
| 2004/0068805 A1 | 4/2004 | Fishman | |
| 2006/0229226 A1 | 10/2006 | Giniger | |
| 2008/0031843 A1 | 2/2008 | Aubert | |
| 2010/0135918 A1 * | 6/2010 | Kim et al. | ........................ 424/47 |
| 2010/0236570 A1 * | 9/2010 | Fujinuma et al. | ............. 132/208 |

FOREIGN PATENT DOCUMENTS

| | | |
|---|---|---|
| EP | 1 295 588 A1 | 3/2003 |
| EP | 1 321 128 A2 | 6/2003 |
| EP | 1 704 897 A1 | 9/2006 |
| GB | 1 125 528 A | 8/1968 |
| WO | 2011/042759 A2 | 4/2011 |

OTHER PUBLICATIONS

International Search Report mailed Feb. 5, 2013, issued in corresponding International Application No. PCT/EP2012/071253, filed Oct. 26, 2012, 3 pages.

* cited by examiner

*Primary Examiner* — Eisa Elhilo
(74) *Attorney, Agent, or Firm* — Christensen O'Connor Johnson Kindness PLLC; Juan Zheng; Llewellyn Lawson

(57) ABSTRACT

The present invention relates to a multi-compartment device or kit for dyeing keratinous fibers, in particular human keratinous fibers, such as the hair, comprising a first compartment including a dyeing composition (A) comprising one or more oxidation dyes and one or more alkaline agents and a second compartment including a composition (B) comprising one or more oxidizing agents; the said device also comprising one or more self-foaming agents having a boiling point of at least 1° C. present in at least one of the compositions (A) and/or (B). The invention also relates to a ready-for-use self-foaming dyeing composition and to a method for dyeing keratinous fibers employing this composition.

17 Claims, No Drawings

DEVICE FOR SELF-FOAMING OXIDATION DYEING, READY-FOR-USE SELF-FOAMING COMPOSITION AND METHOD FOR DYEING KERATINOUS FIBRES

The present invention relates to the field of the dyeing of keratinous fibres and more particularly to the field of hair dyeing.

The present invention relates to a multi-compartment device or kit for dyeing keratinous fibres, in particular human keratinous fibres, such as the hair, comprising a first compartment including a dyeing composition (A) comprising one or more oxidation dyes and one or more alkaline agents and a second compartment including a cosmetic composition (B) comprising one or more oxidizing agents; the said device also comprising one or more self-foaming agents present in at least one of the said compositions (A) and/or (B).

The invention also relates to a self-foaming dyeing composition comprising one or more oxidation dyes, one or more alkaline agents and one or more self-foaming agents in the presence of a specific oxidizing agent.

The invention also relates to a method for dyeing keratinous fibres employing, on the said fibres, the said self-foaming dyeing composition.

It is known to confer "permanent" colorations with dyeing compositions comprising oxidation dye precursors, generally known as oxidation bases, such as ortho- or para-phenylenediamines, ortho- or para-aminophenols and heterocyclic compounds. These oxidation bases are colourless or weakly coloured compounds which, in combination with oxidizing products, can give rise to coloured compounds by an oxidative condensation process.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds, such as indole compounds. The variety of the molecules used as oxidation bases and couplers allows a rich palette of colours to be obtained.

This oxidation dyeing method thus consists in applying, to the keratinous fibres, oxidation bases or a mixture of oxidation bases and couplers with hydrogen peroxide ($H_2O_2$ or aqueous hydrogen peroxide solution), as oxidizing agent, in leaving to diffuse, and in then rinsing the fibres. The colorations which result therefrom are generally permanent, strong and resistant to external agents, in particular to light, bad weather, washing operations, perspiration and rubbing actions.

However, the colorations, in particular "permanent" colorations, often remain difficult to maintain over time. Specifically, it is often recommended to treat the head of hair regularly, for example every month, in order to maintain the coloration in order to see to it that the head of hair retains, in its entirety, its acquired colour for as long as possible.

The function of such a maintenance is first to treat the uncoloured roots as they are generally visible in comparison with the remainder of the head of hair. This treatment can prove to be particularly necessary in the case where the model exhibits white hairs which she wishes to conceal. Another function of this maintenance is to treat the lengths, which can become partially faded over time, in order for the latter to exhibit the same colour as the roots. Finally, such a maintenance can also be used to treat the ends, in particular in the case of long or damaged hair, as the ends, as a result of their porosity, can lose their colour more rapidly than the lengths.

Furthermore, the majority of oxidation dyeing methods employ a lightening system, that is to say that they are carried out in the presence of an oxidizing agent in an alkaline medium, in order to obtain a homogeneous coloration resulting in a good level of coverage of the white hairs. The result of this is that it is all the more difficult to maintain such a coloration in order for it to retain its homogeneous appearance.

In order to successfully carry out such a maintenance, the hair stylist or the user generally employs a method consisting, in a first step, in applying with precision a dyeing composition to the roots, in order to conceal their colour, and in then applying, before the end of the leave-in time, a fresh amount of the said composition on the lengths, in order to obtain a homogeneous colour. Finally, the hair stylists also treat the ends of the fibres, generally by massaging them, so as to ensure that the dyeing composition suitably impregnates the ends. The result of this is that this method, targeted at maintaining the coloration, can prove to be lengthy and problematic to carry out.

The current rheology of dyeing compositions tends, even so, to facilitate these various operations. For example, the use of dyeing compositions in the cream or gel form using tools, such as a brush, a fine comb or a packaging article equipped with a nozzle in the form of a fine stiff comb, makes it possible to more easily reach the uncoloured roots and to treat them more efficiently.

However, it still remains difficult and rather impractical to apply these compositions, in particular to the roots, which tends to put off some users. Furthermore, it is not obvious to obtain roots of the same colour as the lengths. As a result of all these disadvantages, a number of users put back the maintenance dates, which has the disadvantage of worsening the situation as the roots become ever more visible and the ends even more faded.

Other approaches involving, for their part, the use of dyeing compositions in the foam form have also been provided in order to facilitate treatments of this type.

However, it has been observed that this technology also exhibited a number of disadvantages. First of all, it is not easy to apply a foam to the roots. This is because the volume occupied by the foam does not make it possible to easily reach the roots without the product becoming attached to the lengths. Consequently, the result with regard to the roots does not always correspond to the expectations of the user. Furthermore, the volume occupied by the foam gives the user the impression, wrongly, that the amount of the dyeing composition applied to the head of hair is sufficient to obtain a satisfactory level of coloration. In point of fact, after having applied the dyeing composition, it has been observed that the level of coloration and of coverage of the hairs is most of the time inadequate, in particular in the case of white hairs which it is desired to conceal or of lightening or bleaching treatments. Finally, the dyeing compositions in the foam form have a tendency to change in the direction of more fluid compositions and to flow. Thus, when the volume of the foam diminishes, some parts of the head of hair are less well treated than others, which results in a lack of homogeneity in the coloration obtained. Furthermore, poor adhesion of the foams to the head of hair has often been found, with departures in packets, which can cause stains on the clothing.

There thus exists a real need to employ, on keratinous fibres, dyeing compositions capable of conferring satisfactory colorations, in particular in terms of strength, chromaticity and/or resistance, the maintenance problems of which are minimized.

This aim is achieved by the present invention, which has in particular as subject-matter a multi-compartment device or kit for dyeing keratinous fibres, in particular human keratinous fibres, such as the hair, comprising:

i) a first compartment including a composition (A) comprising one or more oxidation dyes and one or more alkaline agents,
ii) a second compartment including a composition (B) comprising one or more oxidizing agents, and
iii) one or more self-foaming agents having a boiling point of at least 1° C. being present in at least one of the compositions (A) and/or (B).

In accordance with the present invention, the self-foaming agent or agents are:

either formulated in the dyeing composition (A), that is to say is or are present in the first compartment of the device,
or formulated in the cosmetic composition (B), that is to say is or are present in the second compartment of the device,
or formulated in the cosmetic compositions (A) and (B), that is to say is or are present in both compartments of the device.

The composition or compositions (A) and/or (B), which comprise one or more self-foaming agents, correspond to cosmetic compositions known as "self-foaming".

The composition (A) can thus be a self-foaming dyeing composition and the composition (B) can be a self-foaming oxidizing composition.

Furthermore, the cosmetic compositions (A) and (B) are mixed with one another at the outlet of the device according to the invention to form a "ready-for-use self-foaming" dyeing composition.

The term "self-foaming composition" is understood to mean, within the meaning of the present invention, a composition which is provided, at the outlet of the packaging article, in a non-expanded or weakly expanded form and which, by the presence of the foaming agent or agents, slowly changes to an expanded form, that is to say that foam is produced, spontaneously after a certain time or under the action of an external stimulus, for example by massaging the composition, by radiation (light or infrared), by increasing the temperature or by modifying the pressure. The volume of the self-foaming composition then significantly increases as a function of the time or under the action of a stimulus to change from a non- or weakly expanded state to an expanded state.

The expansion of the composition is triggered either from a certain period of time, namely the time sufficient to allow the self-foaming agent to evaporate when the latter is a volatile hydrocarbon having a boiling point close to ambient temperature, or under the effect of a stimulus, for example via an increase in the temperature which brings about the evaporation of the self-foaming agent when the latter exhibits a boiling point greater than ambient temperature.

In other words, the self-foaming composition does not create foam at the outlet of the packaging article but it creates a foam either at the end of a certain time after having been exposed to ambient temperature, or after having been exposed to an increase in temperature or another stimulus.

In particular, when the self-foaming composition is provided at the start in a non- or weakly expanded form, it exhibits a density preferably of greater than 0.5. The composition then retains this weakly expanded form for a certain period of time, for example about 15 seconds, during which the density remains relatively constant. When the self-foaming composition changes in the direction of an expanded form, the density of the composition can thus decrease by a factor of 2 in 15 seconds and by a factor of 4 in one minute, either spontaneously or under the effect of a stimulus.

The term "composition having a non- or weakly expanded form" is understood to mean, within the meaning of the present invention, a fluid composition which is not in the foam form at ambient temperature (25±2° C.), that is to say a composition which has a density of greater than 0.5.

The term "expanded composition" is understood to mean, within the meaning of the present invention, a composition which is in the foam form after having been exposed to ambient temperature (25±2° C.) or after having been exposed to an increase in temperature or to another external stimulus (radiation or friction of the composition), that is to say a composition having a density of less than 0.5 and preferably of less than 0.3, better still of less than 0.2.

The ready-for-use self-foaming dyeing composition resulting from the mixing of the cosmetic compositions (A) and (B) is thus applied to the keratinous fibres in a form which is relatively unexpanded, indeed even non-expanded, and subsequently changes in the direction of an expanded form, either spontaneously at the end of a certain time or under the action of a stimulus.

The ready-for-use self-foaming dyeing composition can thus be easily applied to the whole of the head of hair without seeking to carry out a precise application, in particular at the roots, which makes it easy and practical to use. Thus, the attention of the user can be reduced as the latter does not need to confirm if the composition is applied with precision at each point on the head of hair.

This is because the expansion of the dyeing composition makes it possible to easily surround all of the roots and lengths, which also makes it possible to carry out homogeneous dyeing. In particular, the deployment of the foam makes it possible for the ready-for-use dyeing composition not only to more easily reach the roots but also to treat the lengths, which implies that the roots and lengths can be dyed with the same dyeing composition.

The application of the ready-for-use self-foaming dyeing composition is all the easier as it does not require the use of specific tools, for example a brush, in order to achieve better treatment of the roots.

Furthermore, given that the ready-for-use self-foaming dyeing composition is provided at the start in a non-expanded form, it is easier to control the amount of product to be applied over the whole of the head of hair in order to obtain a satisfactory level of coloration.

In other words, the ready-for-use self-foaming dyeing composition thus makes it possible not only to satisfactorily dye the keratinous fibres but also to result in colorations which are easy to maintain.

The ready-for-use self-foaming dyeing composition obtained subsequent to the mixing of the cosmetic compositions (A) and (B) makes it possible to result in strong and relatively unselective colorations.

The invention also relates to a self-foaming dyeing composition for keratinous fibres comprising one or more oxidation dyes, one or more alkaline agents, one or more self-foaming agents having a boiling point of at least 1° C. and hydrogen peroxide.

The present invention also relates to a method for dyeing keratinous fibres, in particular human keratinous fibres, such as the hair, comprising the application, to the said fibres, of a ready-for-use self-foaming dyeing composition comprising one or more oxidation dyes, one or more alkaline agents and one or more self-foaming agents having a boiling point of at least 1° C. in the presence of hydrogen peroxide for a time sufficient to obtain the expansion of the said composition and to develop the desired coloration.

Other subject-matters and characteristics, aspects and advantages of the invention will become even more clearly apparent on reading the description and the examples which follow.

The composition (A) comprises one or more oxidation dyes.

The oxidation dyes can be chosen from one or more oxidation bases, optionally in combination with one or more couplers.

By way of example, the oxidation bases are chosen from para-phenylenediamines, bis(phenyl)alkylenediamines, para-aminophenols, ortho-aminophenols, heterocyclic bases and their addition salts.

Mention may be made, among para-phenylenediamines, by way of example, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene and 3-hydroxy-1-(4'-aminophenyl)pyrrolidine and their addition salts with an acid.

Preference is particularly given, among the abovementioned para-phenylenediamines, to para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and their addition salts with an acid.

Mention may be made, among bis(phenyl)alkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and their addition salts.

Mention may be made, among para-aminophenols, by way of example, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol and their addition salts with an acid.

Mention may be made, among ortho-aminophenols, by way of example, of 2-aminophenol, 2-amino-5-methylphenol, 2-amino-6-methylphenol, 5-acetamido-2-aminophenol and their addition salts.

Mention may be made, among heterocyclic bases, by way of example, of pyridine derivatives, pyrimidine derivatives and pyrazole derivatives.

Mention may be made, among pyridine derivatives, of the compounds described, for example, in Patents GB 1 026 978 and GB 1 153 196, such as 2,5-diaminopyridine, 2-(4-methoxyphenyl)amino-3-aminopyridine, 3,4-diaminopyridine and their addition salts.

Other pyridine oxidation bases of use in the present invention are the 3-aminopyrazolo[1,5-a]pyridine oxidation bases or their addition salts described, for example, in Patent Application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and their addition salts.

Mention may be made, among pyrimidine derivatives, of the compounds described, for example, in Patents DE 2359399, JP 88-169571, JP 05-63124 and EP 0 770 375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Mention may be made, among pyrazole derivatives, of the compounds described in Patents DE 3843892 and DE 4133957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-(hydroxymethyl)-1-methylpyrazole, 4,5-diamino-3-(hydroxymethyl)-1-isopropylpyrazole, 4,5-diamino-3-methyl-1-isopropylpyrazole, 4-amino-5-(2'-amino ethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1- methylpyrazole and their addition salts. Use may also be made of 4,5-diamino-1-(β-methoxyethyl)pyrazole.

Use will preferably be made of a 4,5-diaminopyrazole and more preferably still of 4,5-diamino-1-(β-hydroxyethyl)pyrazole and/or one of its salts.

Mention may also be made, as pyrazole derivatives, of diamino-N,N-dihydropyrazolopyrazolones and in particular those described in Application FR-A-2 886 136, such as the following compounds and their addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or one of its salts.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or one of their salts.

The coupler or couplers are advantageously chosen from those conventionally used for the dyeing of keratinous fibres.

Mention may in particular be made, among these couplers, of meta-phenylenediamines, meta-aminophenols, meta-diphenols, naphthalene couplers, heterocyclic couplers and their addition salts.

Mention may be made, by way of example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzo-morpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1H-3-methylpyrazol-5-one, 1-phenyl-3-methyl-pyrazol-5-one, 2,6-dimethylpyrazolo[1,5-b][1,2,4]triazole, 2,6-dimethyl[3,2-c][1,2,4]triazole, 6-methylpyrazolo[1,5-a]benzimidazole, their addition salts with an acid, and their mixtures.

In general, the addition salts of the oxidation bases and couplers which can be used in the context of the invention are chosen in particular from the addition salts with an acid, such as the hydrochlorides, hydrobromides, sulfates, citrates, succinates, tartrates, lactates, tosylates, benzenesulfonates, phosphates and acetates.

The oxidation base or bases each advantageously represent from 0.0001% to 10% by weight, with respect to the total weight of the composition, preferably from 0.005% to 5% by weight, with respect to the total weight of the cosmetic composition (A).

The content of coupler(s), if it (they) is (are) present, each advantageously represents from 0.0001% to 10% by weight, with respect to the total weight of the composition, preferably from 0.005% to 5% by weight, with respect to the total weight of the cosmetic composition (A).

The composition (A) also comprises one or more alkaline agents.

In particular, the alkaline agents are chosen from i) aqueous ammonia, ii) alkanolamines, such as mono-, di- and triethanolamines and their derivatives, iii) oxyethylenated and/or oxypropylenated ethylenediamines, iv) inorganic or organic hydroxides, v) alkali metal silicates, such as sodium metasilicates, vi) amino acids, preferably basic amino acids, such as arginine, lysine, ornithine, citrulline and histidine, and vii) the compounds of following formula (I):

in which:
W is a divalent $(C_1-C_8)$alkylene group, preferably a propylene group, which is optionally substituted, in particular by a hydroxyl group or a $C_1-C_4$ alkyl radical, and
$R_a$, $R_b$, $R_c$ and $R_d$, which are identical or different, represent a hydrogen atom or a $C_1-C_4$ alkyl or hydroxy($C_1-C_4$)alkyl radical.

The inorganic or organic hydroxides, in particular the inorganic or organic hydroxides, are preferably chosen from i) hydroxides of an alkali metal, ii) hydroxides of an alkaline earth metal, such as sodium hydroxide or potassium hydroxide, iii) hydroxides of a transition metal, such as hydroxides of metals from Groups III, IV, V and VI, and iv) hydroxides of lanthanides or of actinides, quaternary ammonium hydroxides and guanidinium hydroxide.

The hydroxide can be formed in situ, such as, for example, guanidine hydroxide, by reaction of calcium hydroxide and guanidine carbonate.

Preferably, the alkaline agents used in the cosmetic composition (A) are chosen from aqueous ammonia, alkanolamines, in particular mono-, di- and triethanolamines, or silicates, more preferably still alkanolamines.

The alkaline agent(s) preferably represent from 0.01% to 30% by weight and more preferably from 0.1% to 20% by weight, with respect to the total weight of the composition (A).

The pH of the cosmetic composition (A) is preferably greater than 7 and in particular varies from 7.1 to 11.

In accordance with the device of the present invention, the cosmetic composition (B) comprises one or more oxidizing agents.

Preferably, the oxidizing agent or agents are chosen from hydrogen peroxide, urea hydrogen peroxide, alkali metal bromates or ferricyanides, peroxygenated salts, such as, for example, alkali metal or alkaline earth metal persulfates, perborates and percarbonates, and also peracids and their precursors.

More preferably still, the oxidizing agent or agents are chosen from hydrogen peroxide, urea hydrogen peroxide or alkali metal bromates or ferricyanides.

This oxidizing agent advantageously consists of hydrogen peroxide, in particular in aqueous solution (aqueous hydrogen peroxide solution), the concentration of which can vary, more particularly from 0.1% to 50% by weight, more preferably still from 0.5% to 20% by weight and better still from 1% to 15% by weight, with respect to the oxidizing composition (B).

The oxidizing agent can also comprise, as a function of the desired degree of lightening, an oxidizing agent preferably chosen from peroxygenated salts.

The oxidizing composition (B) can be aqueous or anhydrous. The term "aqueous composition" is understood to mean a composition comprising more than 5% by weight of water, preferably more than 10% by weight of water and more advantageously still more than 20% by weight of water.

Preferably, the oxidizing composition (B) is an aqueous composition.

In accordance with the present invention, one or more self-foaming agents having a boiling point of at least 1° C. is or are employed in the cosmetic composition or compositions (A) and/or (B).

The term "self-foaming agent" is understood to mean, within the meaning of the present invention, a compound which, alone or in interaction with at least one other self-foaming agent, is capable of making possible the generation of a foam with a delayed effect on application starting from the composition in which it is present, this being achieved either spontaneously or under the action of one or more external stimuli.

The term "self-foaming agent" also corresponds to one or more compounds capable of reacting with one another when they are brought into contact to form a gas responsible for the expansion of the composition.

According to a first alternative form of the invention, the self-foaming agent corresponds to a volatile hydrocarbon capable of bringing about the foaming of the cosmetic composition as a result of its evaporation at ambient temperature. In other words, the self-foaming dyeing composition resulting from the mixing of the compositions (A) and (B) starts foaming naturally on application in the absence of an external stimulus.

In accordance with this first alternative form, the self-foaming agent or agents are volatile hydrocarbons chosen from aliphatic $C_4$-$C_6$ hydrocarbons having a boiling point which can range from 1° C. to 28° C. at atmospheric pressure (760 mm of mercury).

Preferably, the self-foaming agents in accordance with this first alternative form are chosen from isopentane, neopentane, and their mixtures, neopentane and isopentane. Preferably, the composition comprises less than 5% by weight, better still less than 1% by weight, of $C_1$-$C_3$ hydrocarbons and more preferably still does not comprise $C_1$-$C_3$ hydrocarbons.

The self-foaming agent may be formulated in a mixture of gas comprising butane or isobutane, especially isobutane.

Preferably, when the self-foaming agent or agents are used in a mixture of gas, the said mixture mainly comprises the self-foaming agent or agents and preferably comprises at least 90% by weight of the self-foaming agent or agents.

In a preferred alternative form, the self-foaming agent, used alone or as a mixture, is isopentane. More preferably, use will be made of an isopentane/isobutane mixture in a ratio by weight ranging from 1/1 to 3/1. In particular, preference is given to the isopentane/isobutane mixtures comprising at least 50% by weight of isopentane.

Preferably, volatile hydrocarbons having a boiling point ranging from 1° C. to 28° C. at atmospheric pressure (760 mm of mercury) are employed in the composition (A).

According to a second alternative form of the invention, the self-foaming agent is a compound capable of bringing about the foaming of a cosmetic composition applied to keratinous fibres as a result of its evaporation brought about by an increase in the temperature of the fibres. In other words, the self-foaming dyeing composition resulting from the mixing of the compositions (A) and (B) starts to foam when the keratinous fibres are subjected to a heat treatment capable of bringing about the evaporation of the self-foaming agent.

In accordance with this second alternative form, the self-foaming agent is a compound which is non-volatile at ambient temperature, such as halogenated or non-halogenated hydrocarbons having a boiling point varying from 30 to 70° C., and which is preferably chosen from halogenated hydrocarbons, such as perfluorobutyl methyl ether or methyl perfluoroisobutyl ether, or non-halogenated hydrocarbons, such as pentane, neohexane or hexane, and halogenated hydrocarbons, such as perfluorobutyl methyl ether or methyl perfluoroisobutyl ether.

Preferably, halogenated or non-halogenated hydrocarbons having a boiling point ranging from 30 to 70° C. are employed in the composition (A).

The presence of the self-foaming agent can induce a thickening nature in the compositions comprising it.

According to a third alternative form of the invention, the self-foaming agent or agents correspond to one or more compounds capable of reacting with one another when they are brought into contact to form a gas responsible for the expansion of the composition.

In particular, the self-foaming agent or agents correspond to two compounds a) and b) capable of reacting with one another to form a gas, which compounds can be employed respectively in the compositions (A) and (B).

They can also be employed in one and the same composition A or B.

In the latter case, the compounds a) and b) can in particular be brought into contact by a rubbing or heating effect in order to form a gas which will bring about the expansion of the composition in the foam form.

In particular, the compounds a) and/or b) can be introduced in thermal thinning formulations or breakable or meltable shells.

According to one embodiment, the compounds a) and b) are introduced in thermal thinning formulations.

In accordance with this embodiment, the thermal thinning formulations become fluid when they are heated, which makes it possible to bring into contact the compounds a) and b) employed in the cosmetic compositions (A) and/or (B), so that they react with one another to form a gas responsible for activating the foam.

In particular, the thermal thinning formulations comprise, for example, compounds which are solid at ambient temperature and liquid when they are heated above their melting point. The thermal thinning formulas can thus comprise waxes.

The waxes can be chosen from carnauba wax, candelilla wax, esparto wax, paraffin wax, ozokerite, vegetable waxes, such as olive tree wax, rice wax, hydrogenated jojoba wax or absolute flower waxes, such as the blackcurrant flower essential wax sold by Bertin (France), or animal waxes, such as beeswaxes or modified beeswaxes (cerabellina); other waxes or waxy starting materials which can be used according to the invention are in particular marine waxes, such as that sold by Sophim under the reference M82, polyethylene waxes or polyolefin waxes in general.

The thermal thinning formulas can also comprise celluloses and cellulose derivatives which form gels at ambient temperature and which become fluid when they are heated.

Alternatively, the thermal thinning formulas can comprise associative polymers, for example branched polysaccharides, which form gels in the presence of salts or alcohols and which become fluid when they are heated. The thermal thinning formulations can exhibit reversible thermally stimulatable gelling/fluidifying properties.

Thus, when the thermal thinning formulations become fluid, the compounds a) and b) employed in the cosmetic compositions (A) and (B) are brought into contact and form a gas responsible for activating the foam.

According to another embodiment, the compounds a) and b) are introduced in shells which can break under the action of shearing or heat.

The shells which can break under the action of shearing the formula or the meltable shells are, for example, composed of polymeric or non-polymeric matrices which encapsulate the compounds a) and/or b). By way of example, they can be encapsulated in an alginate/calcium salts matrix and be introduced in a fatty phase or a W/O or O/W emulsion comprising a large amount of phase capsules of alginates are destroyed and the compounds a) and/or b) are released and brought into contact. The compounds a) and/or b) can also be encapsulated in waxes, themselves emulsified in an aqueous phase or any phase immiscible with the wax at ambient temperature. Once heated, the waxes melt and release the compounds a) and/or b), which are brought into contact.

The compound a), conversely the compound b), can be chosen from carbonates, such as ammonium carbonate, and the compound b), conversely the compound a), can be chosen from acids, such as citric acid.

In particular, the compounds a) and b), respectively chosen from carbonates and acids, can be introduced, one or the other or both, in a shell which can break under the action of shearing or which can be melted.

In this case, the compounds a) and b) react with one another when they are brought into contact to form carbon dioxide.

The compound a), conversely the compound b), can be aqueous hydrogen peroxide solution and the compound b), conversely the compound a), can be a compound which is both an oxidizing agent and a reducing agent, such as manganese or iodine.

In this case, the compounds a) and b) react with one another when they are brought into contact to form oxygen.

The self-foaming agent or agents is or are present in the composition(s) (A) and/or (B) in a content ranging from 0.2% to 50% by weight, preferably in a content ranging from 1% to 10% by weight and more preferentially in a content ranging from 2% to 7% by weight, with respect to the total weight of the composition or compositions (A) and (B).

Preferably, the cosmetic composition comprising the self-foaming agent exhibits an initial viscosity before application of greater than or equal to 1000 cPs, measured at 25° C. at a shear rate of 1 s$^{-1}$. In particular, the cosmetic composition can exhibit a viscosity ranging from 1000 to 1 000 000 cPs, measured at 25° C. at a shear rate of 1 s$^{-1}$.

The viscosity of the cosmetic composition can be determined with a rheometer of RS600 type from Thermoelectron.

Preferably, the self-foaming agent is employed in the composition (A). In other words, the composition (A) is preferably a self-foaming dyeing composition.

The composition (A) and the composition resulting from the mixing of the compositions (A) and (B) preferably comprises, in addition, one or more thickening agents.

Within the meaning of the present invention, the term "thickener" is understood to mean any compound whose presence increases the viscosity of the composition into which it is introduced by at least 25 cPs and preferably 50 cPs at 25° C. and at a shear rate of 1 s$^{-1}$.

The thickening agents can be chosen from inorganic thickening agents and organic thickening agents.

According to one embodiment, the inorganic thickening agents are chosen from organophilic clays, fumed silicas or their mixtures.

The organophilic clay can be chosen from montmorillonite, bentonite, hectorite, attapulgite, sepiolite and their mixtures. The clay is preferably a bentonite or a hectorite.

These clays can be modified with a chemical compound chosen from quaternary ammoniums, tertiary amines, amine acetates, imidazolines, amine soaps, fatty sulfates, alkylarylsulfonates, amine oxides and their mixtures.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; quaternium-18/benzalkonium bentonites, such as those sold under the names Claytone HT and Claytone PS by Southern Clay; quaternium-18 hectorites, such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by Rheox, and Simagel M and Simagel SI 345 by Biophil.

The fumed silicas can be obtained by high-temperature pyrolysis of a volatile silicon compound in an oxyhydrogen flame, producing a finely divided silica. This process makes it possible in particular to obtain hydrophilic silicas which exhibit a large number of silanol groups at their surface. Such hydrophilic silicas are, for example, sold under the names "Aerosil 130®", "Aerosil 200®", "Aerosil 255®", "Aerosil 300®" and "Aerosil 380®" by Degussa and "Cab-O-Sil HS-5®", "Cab-O-Sil EH-5®", "Cab-O-Sil LM-130®", "Cab-O-Sil MS-55®" and "Cab-O-Sil M-5®" by Cabot.

It is possible to chemically modify the surface of the silica by chemical reaction for the purpose of reducing the number of silanol groups. It is possible in particular to replace silanol groups with hydrophobic groups: a hydrophobic silica is then obtained.

The hydrophobic groups can be:
  trimethylsiloxyl groups, which are obtained in particular by treating fumed silica in the presence of hexamethyldisilazane. Silicas thus treated are known as "Silica silylate" according to the CTFA (6th Edition, 1995). They are sold, for example, under the references "Aerosil R812®" by Degussa and "Cab-O-Sil TS-530®" by Cabot.
  dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th Edition, 1995). They are, for example, sold under the references "Aerosil R972®" and "Aerosil R974®" by Degussa and "Cab-O-Sil TS-610®" and "Cab-O-Sil TS-720®" by Cabot.

The fumed silica preferably exhibits a particle size which can be nanometric to micrometric, for example ranging from approximately 5 to 200 nm.

Preferably, the composition comprises, as inorganic thickeners, a hectorite, an organomodified bentonite or an optionally modified fumed silica.

According to another embodiment, the thickening agents employed in the dyeing composition (A) can be chosen from organic thickening agents.

The organic thickening agents can be chosen from fatty acid amides (coconut monoethanolamide or diethanolamide, oxyethylenated alkyl ether carboxylic acid monoethanolamide), polymeric thickeners, such as cellulose thickeners (hydroxyethylcellulose, hydroxypropylcellulose or carboxymethylcellulose), guar gum and its derivatives (hydroxypropyl guar), gums of microbial origin (xanthan gum, scleroglucan gum), crosslinked homopolymers of acrylic acid or of acrylamidopropanesulfonic acid and associative polymers (polymers comprising hydrophilic regions and hydrophobic regions having a fatty chain (alkyl or alkenyl chain comprising at least 10 carbon atoms) which are capable, in an aqueous medium, of reversibly associating with one another or with other molecules).

According to a specific embodiment, the organic thickener is chosen from cellulose thickeners (hydroxyethylcellulose, hydroxypropylcellulose or carboxymethylcellulose), guar gum and its derivatives (hydroxypropyl guar), gums of microbial origin (xanthan gum, scleroglucan gum) and crosslinked homopolymers of acrylic acid or of acrylamidopropanesulfonic acid, and preferably from cellulose thickeners with in particular hydroxyethylcellulose.

Preferably, the thickening agents used in the cosmetic composition (A) according to the invention are polymeric thickeners more preferably still chosen from cellulose thickening agents, in particular hydroxyalkylcelluloses, especially hydroxyethylcellulose and hydroxypropylcellulose.

The composition (B) can also comprise one or more thickening agents.

The thickening agent or agents can be present in the compositions comprising them in a content ranging from 0.01% to 15% by weight, preferably from 0.05% to 10% by weight and more preferably still from 0.1% to 5% by weight, with respect to the total weight of the composition.

Mention may more particularly be made, among suitable organic solvents, of non-aromatic alcohols, such as ethyl alcohol or isopropyl alcohol, or glycols or glycol ethers, such as, for example, ethylene glycol monomethyl, monoethyl or monobutyl ether, propylene glycol or its ethers, such as, for example, propylene glycol monomethyl ether, butylene glycol, dipropylene glycol and also diethylene glycol alkyl ethers, such as, for example, diethylene glycol monoethyl ether or monobutyl ether, or alternatively polyols, such as glycerol. Polyethylene glycols and polypropylene glycols, and mixtures of all these compounds, can also be used as solvent.

The normal solvents described above, if they are present, usually represent from 0.1% to 30% by weight and more preferably from 0.5% to 20% by weight, with respect to the total weight of the composition comprising them.

The compositions (A) and (B) can also comprise one or more surfactants.

Preferably, the surfactant or surfactants are chosen from anionic surfactants, which are synthetic or natural, or non-ionic surfactants.

Mention may be made, as examples of synthetic anionic surface-active agents which can be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates, salts of alkyl monoesters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids; and the corresponding non-salified forms of all these compounds, the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surface-active agent or agents is (are) in the salt form, it (they) can be chosen from the alkali metal salts, such as the sodium or potassium salt and preferably the sodium salt, the ammonium salts, the amine salts and in particular the aminoalcohol salts, or the alkaline earth metal salts, such as the magnesium salt.

Mention may in particular be made, as examples of aminoalcohol salts, of mono-, di- and triethanolamine salts, mono-, di- or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline earth metal salts, in particular sodium or magnesium salts.

The anionic surfactants which are optionally present can be mild anionic surfactants, that is to say without a sulfate functional group.

Mention may in particular be made, as regards the mild anionic surfactants, of the following compounds and their salts, and also their mixtures:
  polyoxyalkylenated alkyl ether carboxylic acids,
  polyoxyalkylenated alkylaryl ether carboxylic acids,
  polyoxyalkylenated alkylamido ether carboxylic acids, in particular those comprising from 2 to 50 ethylene oxide groups,
  alkyl-D-galactosideuronic acids,
  acyl sarcosinates, acyl glutamates, and
  alkylpolyglycoside carboxylic esters.

Use may very particularly be made of polyoxyalkylenated alkyl ether carboxylic acids, such as, for example, lauryl ether carboxylic acid (4.5 EO), for example sold under the name Akypo RLM 45 CA from Kao.

The natural anionic surfactants are water-soluble soaps.

Preferably, the water-soluble soap is a water-soluble fatty acid salt. Such soaps are prepared, for example, by reacting a base, such as triethanolamine, directly with one or more fatty acids, such as a saturated or unsaturated $C_8$-$C_{22}$ fatty acid, or mixtures of these acids, such as stearic acid, lauric acid, palmitic acid or oleic acid, preferably stearic acid and palmitic acid, or mixtures of these acids.

Preferred soaps according to the invention comprise water-soluble stearates, myristates and palmitates, such as soluble amine soaps of stearic or palmitic acids which are commercially available. The triethanolamine salts of these acids are more particularly preferred.

A water-soluble soap which is particularly preferred according to the invention is triethanolamine palmitate.

The presence of a water-soluble soap makes it possible in particular to thicken the ready-for-use self-foaming dyeing composition which will become increasingly fluid as a function of the expansion of the composition. Thus, the ready-for-use self-foaming composition is easier to spread.

The non-ionic surfactants are chosen more particularly from mono- or polyoxyalkylenated or mono- or polyglycerolated non-ionic surfactants. The oxyalkylene units are more particularly oxyethylene or oxypropylene units, or their combination, preferably oxyethylene units.

Mention may be made, as examples of oxyalkylenated non-ionic surfactants, of:

oxyalkylenated ($C_8$-$C_{24}$)alkylphenols, oxyalkylenated, saturated or unsaturated and linear or branched $C_8$-$C_{30}$ alcohols, oxyalkylenated, saturated or unsaturated and linear or branched $C_8$-$C_{30}$ amides, esters of saturated or unsaturated and linear or branched $C_8$-$C_{30}$ acids and of polyethylene glycols, polyoxyethylenated esters of saturated or unsaturated and linear or branched $C_8$-$C_{30}$ acids and of sorbitol, oxyethylenated and saturated or unsaturated vegetable oils, condensates of ethylene oxide and/or of propylene oxide, inter alia, alone or as mixtures.

The non-ionic surfactants exhibit a number of moles of ethylene oxide and/or of propylene oxide of between 1 and 100, preferably between 2 and 50. Advantageously, the non-ionic surfactants do not comprise oxypropylene units.

In accordance with a preferred embodiment of the invention, the oxyalkylenated non-ionic surfactants are chosen from oxyethylenated $C_8$-$C_{30}$ alcohols and polyoxyethylenated esters of saturated or unsaturated and linear or branched $C_8$-$C_{30}$ acids and of sorbitol.

Use is preferably made, as examples of mono- or polyglycerolated non-ionic surfactants, of mono- or polyglycerolated $C_8$-$C_{40}$ alcohols.

In particular, the mono- or polyglycerolated $C_8$-$C_{40}$ alcohols correspond to the following formula:

$$RO-[CH_2-CH(CH_2OH)-O]m\text{-}H$$

in which R represents a linear or branched $C_8$-$C_{40}$, preferably $C_8$-$C_{30}$, alkyl or alkenyl radical and m represents a number ranging from 1 to 30 and preferably from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohols may coexist in the form of a mixture.

Use is more particularly made, among the mono- or polyglycerolated alcohols, of the $C_8/C_{10}$ alcohol comprising 1 mol of glycerol, the $C_{10}/C_{12}$ alcohol comprising 1 mol of glycerol and the $C_{12}$ alcohol comprising 1.5 mol of glycerol.

The surfactant content of the compositions (A) or (B) can vary from 0.1% to 50% by weight and preferably from 0.5% to 30% by weight, with respect to the weight of the composition.

The cosmetic composition (B) can additionally comprise one or more acidifying agents.

Mention may be made, among the acidifying agents, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

The pH of the cosmetic composition (B) is generally less than 7.

The compositions (A) and (B) according to the invention can also comprise various conventional adjuvants well-known in the art, such as anionic, cationic, non-ionic, amphoteric or zwitterionic polymers or their mixtures; polyols; fatty acids; antioxidants; penetrating agents; sequestering agents; fragrances; dispersing agents; film-forming agents; ceramides; preservatives; opacifying agents; or cationic surfactants.

According to one embodiment, the device according to the present invention can be composed of two bottles capable of pressurizing the compositions (A) and (B) described above, one of the two compositions comprising one or more propellants.

In accordance with this embodiment, each bottle is provided with an orifice connected to an outlet tube capable of conveying the composition (A) or (B) outside the said bottle towards a single tube which can be provided with a valve and a push button. In other words, the ready-for-use self-foaming dyeing composition is produced by causing the compositions (A) and (B) according to the invention to converge towards the single tube under the effect of the pressure.

In accordance with this embodiment, the dyeing composition (A) preferably comprises the self-foaming agent, in particular in the form of a liquefied gas, especially a volatile hydrocarbon having a boiling point which can range from 1° C. to 28° C., such as isopentane.

According to one embodiment, the compartments of the device according to the invention correspond to two bags capable of pressurizing the compositions (A) and (B).

The pressurization of the compositions (A) and (B) is exerted in particular by the walls forming the bags of the device.

In accordance with this embodiment, the compartments in the bag form can comprise closed orifices not connected to one another or open orifices connected to one another via a mixer.

In the case where the compartments in the bag form are not connected to one another, the user can himself mix the two compositions (A) and (B) in order to obtain a ready-for-use self-foaming dyeing composition.

In the case where the compartments in the bag form are connected to one another via a mixer, the compositions (A) and (B) are mixed in order to obtain a ready-for-use self-foaming dyeing composition.

Furthermore, in the case where the self-foaming agent is found formulated either in the first compartment or in the second compartment, use may be made of different methods in order to compress the compartment in the bag form not comprising the said self-foaming agent or agents.

The pressurization of the compartment not comprising the said self-foaming agent or agents can be carried out mechanically via an object which makes it possible to tighten the bag, for example a screw.

The pressurization of the compartment not comprising the said self-foaming agent or agents can be carried out via a gas which surrounds the said compartment and exerts a pressure on its walls in order to compress the cosmetic composition (A) or (B).

According to a specific embodiment of this general form, the device according to the present invention can be composed of two jacketed aerosol devices.

In accordance with this embodiment, first, the dyeing composition (A) as described above, additionally comprising one or more self-foaming agents, is introduced into the central part of a first jacketed aerosol device and a propellant is introduced into the external casing of the device, which is separated from the central part by a compressible and impermeable membrane.

Secondly, the composition (B) as described above is introduced into the central part of a second jacketed aerosol device and a propellant is introduced into the external casing of the device, which is also separated from the central part by a compressible and impermeable membrane.

The result of this is that the compositions (A) and (B) are packaged in two separate aerosol devices. Each aerosol device comprises an outlet orifice.

The outlet orifices of the aerosol devices can be connected to one another via a single outlet tube comprising means capable of mixing the compositions (A) and (B). A ready-for-use self-foaming dyeing composition is obtained at the outlet of the device as described.

According to another specific embodiment of the invention, the device according to the invention can comprise a first compartment in the bag form comprising the said composition (A) additionally comprising one or more self-foaming agents and a second compartment in the bag form comprising the said composition (B), the walls of the said compartment being compressed by the presence of a gas surrounding the compartment.

The pressurization of the compartment not comprising the said self-foaming agent or agents can be carried out by virtue of the presence of a propellant gas, such as dimethyl ether, present in the cosmetic composition not comprising the self-foaming agent.

According to another embodiment, the first compartment can be a container which comprises the dyeing composition (A) comprising the self-foaming agent and which is capable of receiving a pressurized gas and a second compartment comprising a composition (B) comprising one or more oxidizing agents and a pressurized gas.

In accordance with this embodiment, the pressurized gas and the composition (B) are introduced inside the container. In particular, a device used in hairdressing salons can be provided with a gas feeder which makes it possible to pressurize the container.

The present invention also relates to a ready-for-use self-foaming dyeing composition comprising one or more oxidation dyes, one or more alkaline agents, one or more self-foaming agents as previously described and hydrogen peroxide.

The present invention also relates to a method for dyeing keratinous fibres, in particular human keratinous fibres, such as the hair, comprising the application, to the said fibres, of this ready-for-use self-foaming dyeing composition for a time sufficient to obtain the expansion of the said composition and to develop the desired coloration.

In particular, the ready-for-use self-foaming dyeing composition is applied, preferably in the form of knobs, to the keratinous fibres and then there is a wait for the expansion of the said composition or the expansion of the said composition is activated with a stimulus, for example by increasing the temperature, depending on the type of self-foaming agents employed.

The leave-in time after application preferably varies from 1 to 90 minutes, more preferably from 5 to 60 minutes and more preferably still from 10 to 30 minutes.

When a thermal stimulus is applied, in particular when the ready-for-use self-foaming dyeing composition comprises a self-foaming agent chosen from halogenated or non-halogenated hydrocarbons having a boiling point varying from 30 to 60° C., the said composition is applied to the keratinous fibres and, after an optional leave-in time, the said fibres are subjected to a heat treatment at a temperature which can range from 30 to 80° C. in order to obtain the expansion of the said composition, that is to say to activate the deployment of the foam.

In practice, this operation can be carried out using a hair-styling hood, a hair dryer, an infrared ray dispenser and other conventional heating appliances.

According to a specific embodiment, the ready-for-use self-foaming dyeing composition is applied to the keratinous fibres, then the keratinous fibres are covered with an open or closed wrapping system, for example a plastic bag, and then there is a wait for the expansion of the said dyeing composition or the expansion of the said dyeing composition is activated.

According to another specific embodiment, the keratinous fibres are covered with an open wrapping system, then the ready-for-use self-foaming dyeing composition is applied via the opening and then there is a wait for the expansion of the said dyeing composition or the expansion of the said dyeing composition is activated.

The wrapping system makes it possible to prevent the ready-for-use self-foaming dyeing composition from running over the clothing and causing stains.

According to one embodiment, the cap can delimit compartments in which the cosmetic compositions (A) and (B) are placed.

The ready-for-use self-foaming dyeing composition can optionally be applied via a spatula, an applicator comb or others.

The invention also relates to a dyeing cosmetic composition comprising one or more oxidation dyes, one or more alkaline agents, one or more thickening agents and one or more self-foaming agents.

Preferably, the hydrogen peroxide content is greater than or equal to 0.3% by weight and preferably ranges from 0.3% to 10% by weight, with respect to the total weight of the composition.

The examples which follow serve to illustrate the invention without, however, exhibiting a limiting nature.

EXAMPLES

Example 1

The following dyeing composition is prepared from the ingredients indicated in the table below, the amounts of which are expressed as percent by weight, with respect to the total weight of the composition, unless otherwise indicated.

| Composition A | |
|---|---|
| Stearic acid | 5 |
| Palmitic acid | 5 |
| Triethanolamine | 5.55 |
| Oleyl alcohol polyethylene glycol ether (20 EO), sold under the name Brij 98 by ICI | 2 g |
| Hydroxyethylcellulose, sold under the name Cellosize PCG 10 by Union Carbide | 1.35 g |
| Sorbitol | 2 g |
| Polyethylene glycol, sold under the name Polyox WSR 205 by Union Carbide | 0.5 g |
| para-Phenylenediamine | 0.8 g |
| Resorcinol | 0.8 g |
| Water | 100 |

96 grams of the composition described above are introduced into the central part of a jacketed aerosol device. After crimping on the valve, 2.5 grams of isopentane and 1.5 grams of isobutane are introduced. The device is then pressurized by introducing 10 grams of a mixture based on butane, isobutane and propane as propellant into the external casing of the device, which is separated from the central part by a compressible and impermeable membrane.

The following cosmetic composition (B) is also prepared from the ingredients indicated below, the amounts of which are expressed as percent by weight, with respect to the total weight of the composition, unless otherwise indicated.

| Composition B | |
|---|---|
| Oxyethylenated stearyl alcohol (2 EO) | 1.5% |
| Oxyethylenated stearyl alcohol (20 EO) | 1.5% |
| Cetearyl alcohol ($C_{16}/C_{18}$ 50/50) | 15% |
| Hydroxypropyl maize starch phosphate | 1.5% |
| Sorbitol | 4% |
| Tetrasodium pyrophosphate | 0.04% |
| Sodium salicylate | 0.05% |
| Aqueous hydrogen peroxide solution, q.s. | 20 volumes |
| Phosphoric acid, q.s. | pH = 3 |
| Water | 100 g |

100 grams of the composition (B) are introduced into the central part of a jacketed aerosol device. After crimping on the valve, the aerosol device is pressurized by introducing 10 grams of a mixture based on butane, isobutane and propane as propellant into the external casing of the device, which is separated from the central part by a compressible and impermeable membrane.

The two devices comprising the compositions (A) and (B) are subsequently combined by connecting their outlet orifices to a tube with a length of 10 cm and a diameter of 0.8 cm. The outlet pipe comprises means which make it possible to mix the compositions (A) and (B).

After use, a ready-for-use self-foaming dyeing composition is obtained, which is applied to the hair in several portions of 4 grams approximately, the product being concentrated close to the roots. After application, the ready-for-use dyeing composition naturally undergoes an expansion and covers the whole of the hair, in particular at the roots.

Subsequently, approximately 10 minutes after application, the product can be distributed over the lengths. On carrying out the distribution of the product, it is noticed that the expansion continues, which facilitates the operation.

After leaving in at ambient temperature for thirty minutes (counting from the moment of application), the hair is rinsed, shampooed, rinsed again and dried. A homogeneous is obtained with good coverage of the roots.

Example 2

The following dyeing composition is prepared from the ingredients indicated in the table below, the amounts of which are expressed as percent by weight, with respect to the total weight of the composition, unless otherwise indicated.

| Composition | |
|---|---|
| Stearic acid | 5 |
| Palmitic acid | 5 |
| Triethanolamine | 5.55 |
| Oleyl alcohol polyethylene glycol ether (20 EO), sold under the name Brij 98 by ICI | 2 g |
| Hydroxyethylcellulose, sold under the name Cellosize PCG 10 by Union Carbide | 1.35 g |
| Sorbitol | 2 g |
| Polyethylene glycol, | 0.5 g |
| sold under the name Polyox WSR 205 by Union Carbide | |
| para-Phenylenediamine | 0.8 g |
| Resorcinol | 0.8 g |
| Water | 100 |

94 grams of the composition described above are mixed with 6 grams of pentane to produce a self-foaming dyeing composition (C).

The self-foaming dyeing composition (C) is introduced into the central part of a jacketed aerosol device. After crimping on the valve, the aerosol device is pressurized by introducing 10 grams of a mixture based on butane, isobutane and propane as propellant into the external casing of the device, which is separated from the central part by a compressible and impermeable membrane.

The following cosmetic composition (D) is also prepared from the ingredients indicated below, the amounts of which are expressed as percent by weight, with respect to the total weight of the composition, unless otherwise indicated.

| Composition | D |
|---|---|
| Oxyethylenated stearyl alcohol (2 EO), sold under the name Brij S2-SO by Croda | 1.5% |
| Oxyethylenated stearyl alcohol (20 EO), sold under the name Brij S20-PA by Croda | 1.5% |
| Cetearyl alcohol ($C_{16}/C_{18}$ 50/50) | 15% |
| Hydroxypropyl maize starch phosphate | 1.5% |
| Sorbitol | 4% |
| Tetrasodium pyrophosphate | 0.04% |
| Sodium salicylate | 0.05% |
| Aqueous hydrogen peroxide solution, q.s. | 20 volumes |
| Phosphoric acid, q.s. | pH = 3 |
| Water | 100 g |

The composition (C) is then delivered to an intermediate support, such as a bowl or onto a hand.

Mixing is carried out gently with an equal amount of composition (D) and a mixture is obtained, which is applied to the hair in several portions of 4 grams approximately, the product being concentrated on the roots.

The model is then placed under a hairstyling hood. During heating, the composition undergoes an expansion and covers the whole of the hair at the roots.

Subsequently, the product can be easily distributed over the lengths. On again placing the model under the hood, it is noticed that the expansion continues, which facilitates the distribution of the product over the whole of the hair.

Example 3

The following dyeing composition (E) is prepared from the ingredients indicated in the table below, the amounts of which are expressed as percent by weight, with respect to the total weight of the composition, unless otherwise indicated.

| Composition | E |
|---|---|
| Oxyethylenated stearyl alcohol (2 EO), sold under the name Brij S2-SO by Croda | 0.5% |
| Oxyethylenated stearyl alcohol (20 EO), sold under the name Brij S20-PA by Croda | 2% |
| Cetearyl alcohol ($C_{16}/C_{18}$ 50/50) | 10% |
| Cetearyl alcohol (33 EO), sold under the name | 2% |

-continued

| Composition | E |
| --- | --- |
| Simulsol SOL CS by Seppic | |
| Potassium iodide coated at 50% in refined paraffin wax, sold by Avel | 4% |
| Monoethanolamine | 4% |
| para-Phenylenediamine | 0.8 g |
| Resorcinol | 0.8 g |
| Water | 100 g |

The following composition (F) is prepared:

| Composition | F |
| --- | --- |
| Aqueous hydrogen peroxide solution | q.s. 20 volumes |
| Carboxyvinyl polymer | 0.5% |
| Tetrasodium pyrophosphate | 0.04% |
| Sodium salicylate | 0.05% |
| Phosphoric acid | q.s. pH = 3 |
| Water | q.s. 100 g |

At the moment of use, the cosmetic compositions (E) and (F) are mixed in equal amounts on an intermediate support or on the hands and then the mixture obtained is applied to the hair of a model in several portions of 4 grams approximately.

The model is then placed under a hairstyling hood. During heating, the composition undergoes an expansion and covers the whole of the hair at the roots.

Subsequently, the product can be distributed over the lengths. On carrying out the distribution of the product, it is noticed that the expansion continues, which facilitates the distribution of the product over the hair.

Example 4

The following dyeing composition (G) is prepared from the ingredients indicated in the table below, the amounts of which are expressed as percent by weight, with respect to the total weight of the composition, unless otherwise indicated.

| Composition | G |
| --- | --- |
| Palmitic acid | 10% |
| Stearic acid | 3% |
| Triethanolamine | 6.7% |
| Glycerol | 2% |
| Hydroxypropylcellulose | 0.05% |
| PEG 90M | 0.01% |
| Cocamide MEA | 2% |
| Dimethiconol stearate | 0.25% |
| Stearyl heptanoate and stearyl caprolate | 1% |
| para-Phenylenediamine | 2% |
| Resorcinol | 1% |
| Water | 100 g |

96 grams of the composition described above are introduced into the central part of a jacketed aerosol device. After crimping on the valve, 2.5 grams of isopentane and 1.5 grams of isobutane are introduced. The device is then pressurized by introducing 10 grams of a mixture based on butane, isobutane and propane as propellant into the external casing of the device, which is separated from the central part by a compressible and impermeable membrane.

At the moment of application, the composition is applied to the hair, concentrating on the roots. The composition (B) is then applied to the preceding composition, care being taken to apply comparable volumes. It is found that the composition slowly foams and, doing this, becomes more fluid.

Thus, the cosmetic composition spreads while foaming.

The invention claimed is:

1. Multi-compartment device comprising:
   i) a first compartment including a dyeing composition (A) comprising one or more oxidation dyes and one or more alkaline agents,
   ii) a second compartment including a composition (B) comprising one or more oxidizing agents, characterized in that the one or more oxidizing agents are chosen from hydrogen peroxide, urea hydrogen peroxide, alkali metal bromates, alkali metal ferricyanides, peroxygenated salts, peracids and their precursors, and
   iii) one or more self-foaming agents having a boiling point of at least 1° C. present in at least one of the compositions (A) and/or (B).

2. Device according to claim 1, characterized in that the oxidation dye or dyes are chosen from oxidation bases, optionally in combination with one or more couplers.

3. Device according to claim 2, characterized in that the oxidation bases are chosen from ortho- or para-phenylenediamines, double bases, ortho- or para-aminophenols, heterocyclic bases, and the addition salts of these compounds with an acid.

4. Device according to claim 2, characterized in that the coupler or couplers are chosen from meta-phenylenediamines, meta-aminophenols, meta-diphenols, heterocyclic couplers and the addition salts of these compounds with an acid.

5. Device according to claim 1, characterized in that the alkaline agents are chosen from:
   aqueous ammonia,
   alkanolamines,
   oxyethylenated and/or oxypropylenated ethylenediamines,
   inorganic or organic hydroxides,
   alkali metal silicates,
   amino acids, and
   the compounds of following formula (I):

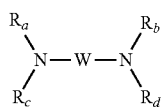

(I)

in which:
   W is a divalent ($C_1$-$C_8$)alkylene group, which is optionally substituted, in particular by a hydroxyl group or a $C_1$-$C_4$ alkyl radical, and
   $R_a$, $R_b$, $R_c$ and $R_d$, which are identical or different, represent a hydrogen atom, a $C_1$-$C_4$ alkyl or hydroxy($C_1$-$C_4$)alkyl radical.

6. Device according to claim 1, characterized in that the self-foaming agent is chosen from volatile aliphatic $C_4$-$C_6$ hydrocarbons having a boiling point which can range from 1° C. to 28° C. at atmospheric pressure (760 mm of mercury).

7. Device according to claim 1, characterized in that the self-foaming agent or agents are chosen from isopentane, neopentane, and their mixtures.

8. Device according to claim 1, characterized in that the self-foaming agent or agents are chosen from halogenated or non-halogenated hydrocarbons having a boiling point varying from 30 to 70° C. at atmospheric pressure (760 mm of mercury).

9. Device according to claim 1, characterized in that the self-foaming agent is chosen from halogenated hydrocarbons and non-halogenated hydrocarbons.

10. Device according to claim 1, characterized in that the self-foaming agents correspond to two compounds a) and b), employed in one or more of the compositions (A) and (B), capable of reacting with one another to form a gas.

11. Device according to claim 10, characterized in that the compound a), conversely the compound b), can be chosen from carbonates, ammonium carbonate, and the compound b), conversely the compound a), can be chosen from acids.

12. Device according to claim 10, characterized in that the compound a), conversely the compound b), is aqueous hydrogen peroxide solution and the compound b), conversely the compound a), is a compound which is both an oxidizing agent and a reducing agent.

13. Self-foaming dyeing composition for keratinous fibres comprising one or more oxidation dyes, one or more alkaline agents and one or more self-foaming agents as defined according to claim 1 and hydrogen peroxide.

14. Composition according to claim 13, characterized in that the hydrogen peroxide content is greater than or equal to 0.3% by weight with respect to the total weight of the composition.

15. Method for dyeing keratinous fibres, comprising the application, to the said fibres, of a ready-for-use self-foaming dyeing composition as defined according to claim 13 for a leave-in time sufficient to obtain the expansion of the said composition and to develop the desired coloration.

16. Device according to claim 9, wherein the halogenated hydrocarbons are selected from the group consisting of perfluorobutyl methyl ester and methyl perfluorobutyl ether.

17. Device according to claim 9, wherein the non-halogenated hydrocarbons are selected from pentane, neohexane, and hexane.

* * * * *